United States Patent [19]

Demhartner

[11] Patent Number: 5,763,331
[45] Date of Patent: Jun. 9, 1998

[54] ABSORBENT COMPOSITE

[76] Inventor: Rudolf Demhartner, Mainzerstr. 7a, 80804 München, Germany

[21] Appl. No.: 389,317

[22] Filed: Feb. 15, 1995

[30] Foreign Application Priority Data

Feb. 15, 1994 [DE] Germany .................. 9402463 U

[51] Int. Cl.$^6$ .............. A61L 15/58; A61L 15/60; B32B 7/12; B32B 7/14
[52] U.S. Cl. .............. 442/68; 442/74; 442/393; 442/394; 442/398; 442/412; 442/417; 604/366; 604/367; 604/370; 604/378
[58] Field of Search .................. 604/370, 366, 604/367, 378, 428; 428/283, 286, 302; 442/68, 74, 393, 394, 398, 412, 417

[56] References Cited

U.S. PATENT DOCUMENTS

| | | |
|---|---|---|
| 4,212,302 | 7/1980 | Karami . |
| 4,297,410 | 10/1981 | Tsuchiya et al. . |
| 4,338,371 | 7/1982 | Dawn et al. . |
| 4,551,191 | 11/1985 | Kock et al. . |
| 5,024,667 | 6/1991 | Malcolm ................ 604/382 |
| 5,160,331 | 11/1992 | Forester et al. . |
| 5,387,208 | 2/1995 | Ashton et al. . |

FOREIGN PATENT DOCUMENTS

| | | |
|---|---|---|
| 0033235 | 8/1981 | European Pat. Off. . |
| 0325416 | 7/1989 | European Pat. Off. . |
| 0401189 | 12/1990 | European Pat. Off. . |
| 0562846 | 9/1993 | European Pat. Off. . |
| 0576738 | 1/1994 | European Pat. Off. . |
| 0631768 | 1/1995 | European Pat. Off. . |
| 3738601 | 5/1989 | Germany . |
| 4207465 | 9/1993 | Germany . |
| 2078527 | 1/1982 | United Kingdom . |
| 9211831 | 7/1992 | WIPO . |
| 9322998 | 11/1993 | WIPO . |

OTHER PUBLICATIONS

*Chemical Abstracts*: 92–393198.

*Chemical Abstracts*: 92–393196.

Primary Examiner—James C. Cannon
Attorney, Agent, or Firm—Robert W. Becker & Associates

[57] ABSTRACT

An absorbent composite, in particular for diapers, sanitary pads or napkins, mattress pads, incontinence briefs and liners or the like, has a support layer onto which a layer of a superabsorbent granular material is applied. A portion of the absorbent material is intimately connected to, particularly glued to, the support layer.

26 Claims, 2 Drawing Sheets

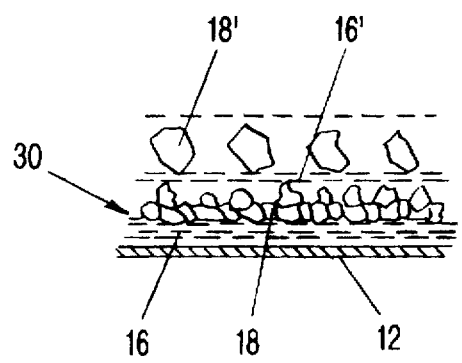
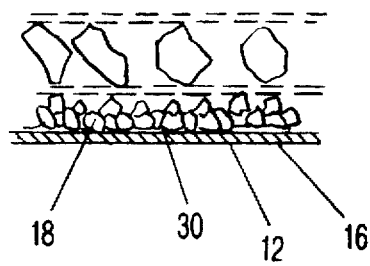
FIG-3a  FIG-3b
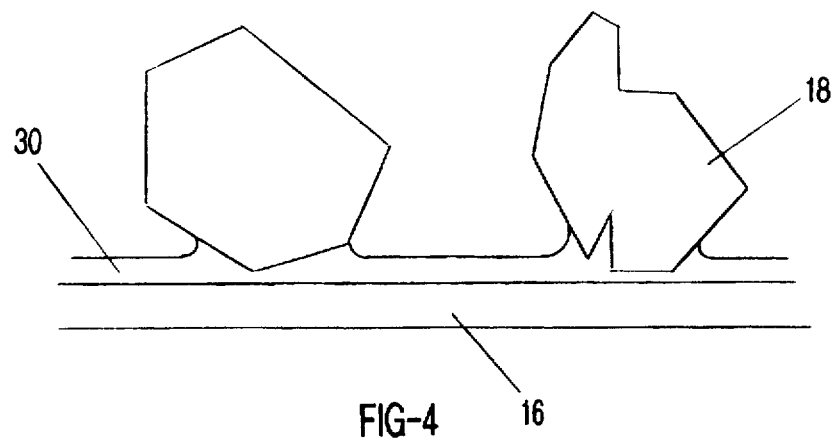
FIG-4
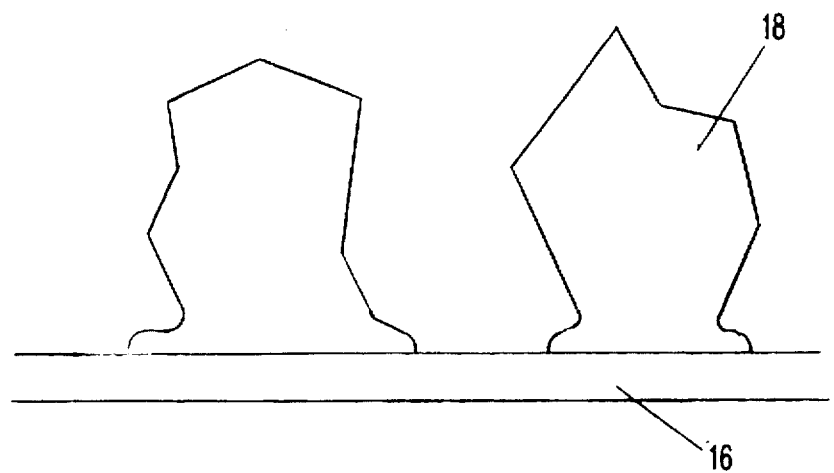
FIG-5

ABSORBENT COMPOSITE

BACKGROUND OF THE INVENTION

The present invention relates to an absorbent composite especially for diapers, mattress pads, sanitary napkins, incontinence briefs and liners, comprising a support layer onto which is applied a layer of absorbent material.

Numerous attempts have been undertaken to produce an absorbent composite, which, on the one hand, is impermeable with respect to the outside, on the other hand, however, gives the impression of being dry on the inside even after being wetted. In order to solve this problem, absorbent bodies, for example, made of polyacrylate, have been used which when wetted with water, urine or other aqueous solutions, for example, with blood, will swell forming a gel and thus exhibit a high degree of absorbent capacity. For this purpose a superabsorbent granular material is used and in this respect reference is, for example, to DE-A1-42 07 465. Granular materials are preferred to compact swelling bodies since the swelling capacity, especially with small grain size, is better due to the increased surface area. In order to improve the swelling capacity and thus the absorbent capacity, it is known to use grain sizes as small as possible adjacent to a layer impermeable to moisture and larger grain sizes preferably on the side facing the body.

Superabsorbent materials are those materials which, upon contact with liquids, imbibe such liquids and thereby form hydrogels. In this manner, liquids discharged into the absorbent composites of the present invention can be absorbed and held by the particles, thereby providing absorbent composites with enhanced absorbent capacity and/or improved liquid retention performance.

The superabsorbent material particles which are employed will generally comprise a substantially water-insoluble, slightly cross-linked, partially neutralized, hydrogel-forming polymer material. Such absorbent materials can be prepared from polymerizable, unsaturated, acid-containing monomers. Thus, such monomers include the olefinically unsaturated acids and anhydrides which contain at least one carbon-to-carbon olefinic double bond. More specifically, these monomers can be selected from olefinically unsaturated carboxylic acids and acid anhydrides, olefinically unsaturated sulfonic acids and mixtures thereof. Another example of such superabsorbent materials are polyacrylates of small grain sizes which are also capable to form hydrogels.

However, especially granular material of a small grain size tends to shift in an undesired manner. If diapers, sanitary napkins or pads or liners and so on were stored in a compactly compressed shape, this danger would be relatively little. However, especially in the case of diapers a certain "fluffiness", i.e. a smooth character of the liner or pad is desired, so that storage in an only slightly compressed form is often preferred. During transport, but also in use, the granules can thus shift.

In order to prevent this, it is known to provide the granules within a compact absorbent body. In this context reference is made, for example, to DE- A1-37 38 601, which shows such an absorbent body covered by a layer of cellulose flocks of a thickness of 0.5 to 10 mm and these cellulose flocks are covered by a layer of nonwoven material.

However, an unequal distribution of the granular bodies cannot be prevented by means of this solution.

The production process provides, granular bodies in the form of relatively sharp-edged grains. In view of the largest possible surface a rather hackly grain structure is even desired. The retaining layer in diapers, pads, etc., by means of which leakage of liquids to the outside is to be prevented, thus must be relatively thick when composites are made of granular material in order to prevent damage to the retaining layer by the granules. However, a relatively thick retaining layer or outer shell is unfavorable, not only with respect to the weight in transport and use but also with respect to disposal.

This effect is especially relevant with respect to sanitary mattress pads and composites for incontinence diapers and liners since the granules before being wetted can behave just like abrasive granules when the patient's movement and weight acts upon the sanitary mattress, pads, etc.

It is therefore an object of this invention to provide an absorbent composite with a comparably thin outer shell, that nevertheless provides an excellent absorbent capacity for liquids while providing a composite that is unaffected even by changing compressive stresses.

SUMMARY OF THE INVENTION

An absorbent composite for absorbing liquids according to the present invention is primarily characterized by:
- a main support layer;
- a layer of absorbent material positioned on the main support layer;
- the absorbent material comprised of a superabsorbent granular component;
- at least a first portion of the superabsorbent granular component being intimately bonded to the main support layer.

Preferably, the absorbent composite further comprises an adhesive for gluing at least the first portion of the superabsorbent granular component to the main support layer.

The adhesive is preferably a spray adhesive.

Advantageously, first the adhesive is applied to the main support layer and the superabsorbent granular component is subsequently placed onto the adhesive on the main support layer.

Alternatively, the adhesive is applied to a layer of the superabsorbent granular component and the main support layer is placed onto the adhesive applied to on the layer of the superabsorbent granular component.

The superabsorbent granular component is preferably comprised of acrylate granules or of a biodegradable material.

Expediently, the adhesive has a reduced moisture contents.

The adhesive forms an adhesive layer and at least the first portion of the superabsorbent granular component is bonded to the adhesive layer. The adhesive layer preferably extends over the entire surface area of the main support layer.

The main support layer is expediently comprised of a material selected from the group consisting of tissue and non-woven material.

The superabsorbent composite may further comprise an intermediate support layer, wherein the first portion of the superabsorbent granular component is bonded to the main support layer and a second portion of the superabsorbent granular component is bonded to the intermediate support layer.

The first portion of the superabsorbent granular component is arranged in a layer such that the granules of the granular component form a single layer within a common plane.

The first portion of the superabsorbent granular component preferably has smaller granules than the second portion of the superabsorbent granular component.

The second portion of the superabsorbent component is glued to the intermediate support layer with an adhesive.

The superabsorbent composite further comprises a cover layer positioned opposite the main support layer for covering the superabsorbent component. The cover layer is preferably comprised of non-woven material comprised of at least 20% of viscose and at most 80% of polypropylene. Alternatively, the non-woven material may be tissue or can be comprised of 100% viscose, that is preferably hydrophilic.

The composite may comprise a cover strip positioned on top of the cover layer. The cover strip is comprised of non-woven material having a hydrophobic inner side facing the cover layer. The non-woven material is preferably comprised of at least 80% of polypropylene and at most 20% viscose. The non-woven material may be comprised of 100% viscose that is preferably hydrophilic.

The absorbent composite further comprises a substantially moisture-impermeable outer shell positioned exterior to the main support layer. The outer shell is expediently made of a material selected from the group consisting of polypropylene and amylose.

The main support layer is substantially moisture-impermeable and made of a material selected from the group consisting of polypropylene and amylose. In this embodiment, there is no need for an outer shell.

Due to the fact that the support layer is intensively connected to the small-size granular component or materials, the risk of damaging the outer surface may surprisingly be reduced drastically even if a very thin retaining layer or outer shell is used. The lowermost granules or grains of the granular component are each fixed on the support layer by gluing with a moisture-reduced spray adhesive so that these grains cannot damage the outer shell. With a correspondingly high density of these lower most granules it is additionally prevented that the adjacent layer of granules can come into contact with the outer surface at all. Surprisingly, penetration of the outer shell is thus impossible, in spite of a relatively small amount of spray adhesive, even in the case of intensive back and forth movement of the patient.

The adhesive can be applied to the support layer and the granules can then be placed thereon. It is also possible to apply the adhesive to a layer of granules and then place the support layer thereon. Another alternative is to soak the support layer with the adhesive and apply the granules on one side and the outer shell on the other side.

According to an alternative embodiment intensive connection is not provided by gluing but by melting the granulated bodies at the side facing the outer shell. They are thus intimately connected by fusing. It is to be understood that this embodiment is only possible if the melting point of the granular bodies is at least somewhat lower than the melting point of the outer shell or at least of the support layer.

According to the invention the lowermost support layer may either consist of non-woven fabric or tissue or may even be formed by the outer shell itself. When being separate from the outer shell the support layer is so dense that, together with the grains of superabsorbent material connected to it, it forms a support structure for the further layers of the composite.

It is to be understood that, if necessary, further layers of the composite may be embodied in a corresponding manner. Instead of a spray adhesive a hot-melt glue can also be used which is compatible with the superabsorbent material, which, however, should not wet the superabsorbent material too much in order not to affect the absorbent capacity thereof.

It is further to be understood that, instead of the preferred polyacrylates with hydroxyl groups, other superabsorbent materials may be used in the same manner.

It is especially advantageous that according to the invention sharp-edged and rough granular bodies may also be used. The individual granular body is smoothly covered by the spray adhesive the side facing outwardly and away from the penetrating moisture. Thus, the risk of scratching is strongly reduced with respect to the outer shell. For example, the support layer that has already been provided with the grains of superabsorbent material can have applied thereto a moisture-reduced spray adhesive from the outside, and immediately subsequently the outer shell may be applied so that the desired intimate connection will result. This process may possibly be improved by applying pressure for a short period. According to another embodiment of the invention, the outer shell is provided with spray adhesive and then the support layer and the superabsorbent grains are placed on the outer shell. Thus, the outer shell and the support layer can be glued together in this manner.

The adhesives to be used should have a reduced moisture contents in order to prevent swelling and absorption of moisture by the granules. The adhesives can be physically or chemically bonding adhesives. The solvents used should not impair the swelling of the granules. Conventional adhesives such as animal-product based adhesive (casein, glutin), plant-based adhesives (starch, dextrin, cellulose ether) or synthetic adhesives (polyacrylic acid-based, polyvinylalcohol-based, polyvinylpyrrolidone-based) can be used with water as a solvent. When using water, the water content of the adhesive should be reduced by 20–80%, especially 40–70% and preferably 60%, relative to the contents of the commercial product. A reduction of the moisture contents to 0 can, of course, be achieved with non-water based adhesives, especially with hot-melt adhesives.

It is possible to use a separate support layer, which is comprised of a non-woven material, or to use the outer shell as a support layer. In the latter case it is to be understood that due to the intimate application of the granulated material, for example, acrylate, a protective layer is formed for the outer shell.

According to the invention, it is especially advantageous that due to the concentration of superabsorbent material adjacent to the cover layer, an especially good absorbent capacity and a dry surface of the diaper or the incontinence brief may be obtained. For this purpose a two-layer structure of the inventive composite, with a smaller grain size adjacent to the outer shell and a larger grain size adjacent to the cover layer, is especially preferred. This embodiment makes possible an absorbent capacity with which only a very small amount of residual moisture can be felt by the patient at the inner surface of the absorbent composite.

According to a further preferred embodiment of the invention, the composite may be covered by a cover strip of non-woven fabric (fibrous web material) with a hydrophobic inner side. By means of this covering strip it is ensured that the liquid will quickly penetrate the composite. After penetration the liquid is effectively prevented from leaking outwardly due to the water-repellent effect of the hydrophobic inner side.

BRIEF DESCRIPTION OF THE DRAWINGS

Further advantages, details and features can be taken from the following description of several embodiments with respect to the drawing in which:

FIGS. 3a, 3b are sections through further embodiments of an inventive absorbent composite;

FIG. 4 is an enlarged view of FIGS. 3a and 3b; and

FIG. 5 is an enlarged sectional view of another embodiment according to the view of FIG. 4.

DESCRIPTION OF PREFERRED EMBODIMENTS

Figure 1:
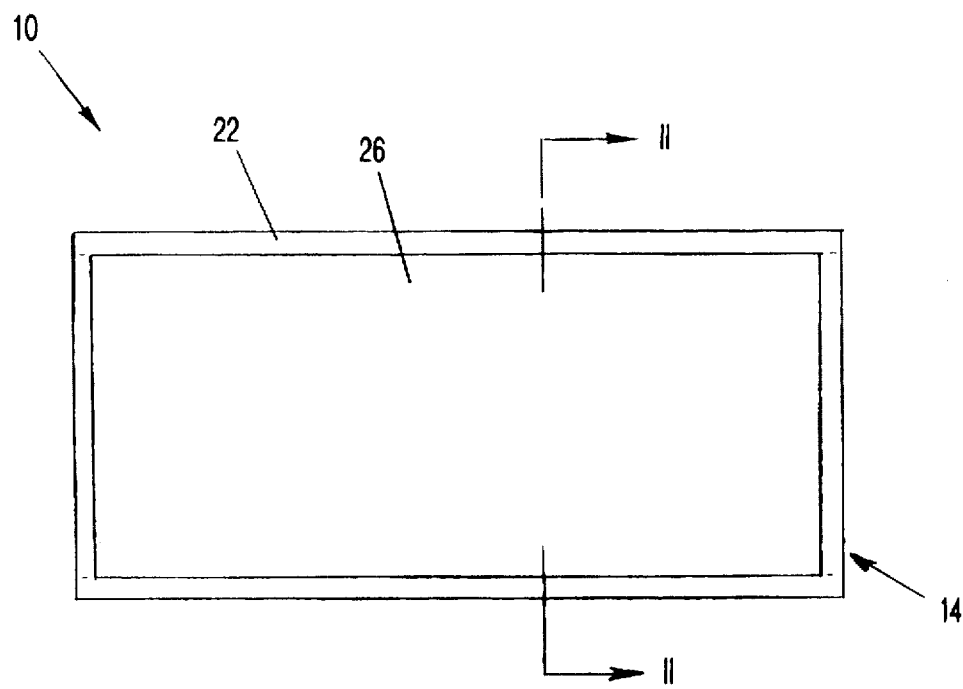
FIG. 1 is a perspective view of an embodiment of an inventive absorbent composite having the shape of an incontinence liner.

FIG. 1 shows an incontinence liner with its outer shell (the side to be placed remote from the patient's skin) facing downward. The outer shell is a plastic sheet that may be breathable and/or textured in order to impart a fabric-like character to the outer surface. However, the outer shell should be impermeable to moisture. The outer shell, for example, consists of polypropylene.

Figure 2:
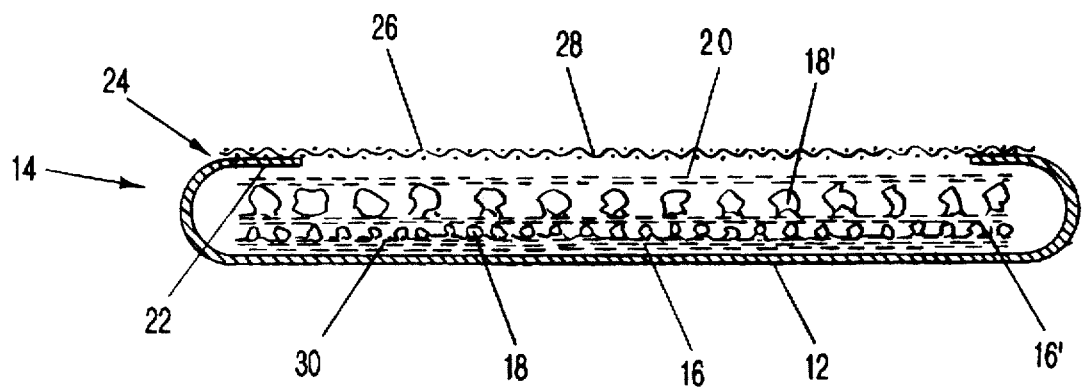
FIG. 2 is a diagrammatic section along line II—II of FIG. 1.

Further, as may be taken from FIG. 2, the absorbent composite 14 comprises a lower main support layer 16 to which a layer 18 of granular acrylate is applied. In order to make the granular material of the layer 18 adhere reliably and non-slidingly to the support layer 16, it is fixed to the support layer 16 by means of a spray adhesive with a very low moisture contents. The fact that the spray adhesive has a low moisture contents will ensure that the granulated material will not swell and absorb moisture already when the adhesive is sprayed onto the material. In order to impart a very low moisture contents to the spray adhesive, it is sprayed onto the support layer 16 via compressed air after being molten as usual. Prior to this the compressed air is past through a drying agent such as silica gel in order to be dried so that only a very small amount of residual moisture of less than 0.5% will remain.

In connection with dried compressed air a hot-melt spray adhesive may also be used. It is to be understood that such an adhesive must both be compatible with the support layer and with the acrylate.

As a support layer 16, a non-woven fabric, weighing, for example, 24 g/m$^2$, or a fine and superabsorbent, wet strength paper material known as "tissue" may be used.

It is to be understood that, instead of substances reacting with urine, other materials may also be used for the support layer, for example, a material comprised of polypropylene and viscose or comprised completely of polypropylene. Thus, the unpleasant odor of the absorbent composite after being wetted with urine will be further reduced.

In the embodiment shown, the layer of the granular component comprises a top layer and a bottom layer 18, 18'. A further intermediate support layer 16' is provided which is somewhat lighter than the main support layer 16 and is arranged on the bottom layer 18 of granulated grains. For example, a non-woven fabric material weighing 18 g/m$^2$ may be employed for the intermediate support layer. A further top layer 18' of granulated acrylate, which has a somewhat larger grain size and thus a relatively smaller surface, is fixed on this support layer 16' with a spray adhesive. It is to be understood that the spray adhesive is applied such that it will not affect the penetration of moisture into the main support layer 16'.

The second layer 18' of superabsorbent granular material is covered by a cover layer 20, for example, of tissue or non-woven fabric weighing 24 g/m$^2$.

Together with a covering strip 26, which may be placed on the cover layer 20, both support layers 16 and 16', the granulate layers 18 and 18' as well as the outer shell 12 form a superabsorbent composite 14. As a semifinished product this composite may be employed for numerous purposes, for example, for producing diapers, sanitary napkins, incontinence briefs and liners or sanitary mattress pads.

As an example, FIG. 1 illustrates such an incontinence liner. As may be taken from FIG. 2, the longitudinal edges 22 of the outer shell 12 may be folded upwardly and inwardly. A cover strip 26 is glued onto the folded edges by means of glue 24 or by hot stamping. The inner side 28 of the cover strip 26 exhibits hydrophobic characteristics. A non-woven material of about 15 g/m$^2$ is suitable for such a cover strip.

The nonwoven material used for the support layers 16, 16', the cover layer 20, and the cover strip 26 preferably consists of a compound of about 80% polypropylene and 20% viscose, however, it may also consist of 100% of polypropylene.

Two further embodiments of a composite according to the invention may be taken from FIGS. 3a and 3b. FIG. 3a, represents one embodiment, showing the way in which spray adhesive 30 embeds the lowermost layer 18 of the granulated bodies and at the same time protects the support layer 16. Beneath the support layer 16 the outer shell 12 is provided. Thus, granules located above the glued-on layer of granular bodies will not come into contact with the support layer 16 and also not with the outer shell 12. Above the layer 18, a further support layer 16' and a further layer of granulated material are provided.

The embodiment illustrated in FIG. 3b shows the outer shell 12 functioning as a support layer 16. The spray adhesive 30 ensures in this case that the lowermost layer of granulated bodies 18 is reliably embedded. Apart from this difference, the embodiment of FIG. 3b corresponds to the one of FIG. 3a.

It may be taken from FIG. 4 that grains of acrylate having edges that are quite sharp may also be used, without having to worry about damaging the outer shell 12 or the support layer 16. The spray adhesive 30 will adapt to the contour of the granular bodies 18 and embed them so that there will be a smooth connection.

In the alternative shown in FIG. 5, the granules of acrylate 18 are virtually molten onto the support layer 16. It is to be understood that this support layer may again be formed by the outer shell 12 if desired. In this embodiment, too, the granules are affixed and will thus form a barrier against the penetration of further granules of acrylate into the outer shell.

It is also possible to use a biodegradable superabsorbent material instead of a superabsorbent material of polyacrylate. For this purpose chemically modified natural substances such as higher sugars or starch products may be employed. In the case of such biodegradable superabsorbent materials, the grain size and thus the relative surface may also be adjusted over a wide range and may accordingly be adapted to the desired specifications.

The present invention is, of course, in no way restricted to the specific disclosure of the specification and drawings, but also encompasses any modifications within the scope of the appended claims.

What I claim is:

1. An absorbent composite for absorbing liquids, said absorbent composite comprising:

a paper or non-woven fabric main support layer;

a layer of absorbent material positioned on said main support layer;

said absorbent material comprising a superabsorbent granular component;

at least a first portion of said superabsorbent granular component being intimately bonded to said main support layer; and an adhesive, applied by spraying from the melt state, for gluing at least said first portion of said superabsorbent granular component to said main support layer;

wherein said adhesive was applied to a layer of said superabsorbent granular component and said main support layer was placed onto said adhesive on said layer of said superabsorbent granular component.

2. An absorbent composite according to claim 1, wherein first said adhesive was applied to said main support layer and said superabsorbent granular component was subsequently placed onto said adhesive on said main support layer.

3. An absorbent composite according to claim 1, wherein said superabsorbent granular component is comprised of acrylate granules.

4. An absorbent composite according to claim 1, wherein said superabsorbent granular component is comprised of a biodegradable material.

5. An absorbent composite according to claim 1, wherein said adhesive has a reduced moisture content.

6. An absorbent composite according to claim 1, wherein said adhesive forms an adhesive layer and wherein at least said first portion of said superabsorbent granular component is bonded to said adhesive layer.

7. An absorbent composite according to claim 6, wherein said adhesive layer extends over the surface area of said main support layer.

8. An absorbent composite according to claim 1, wherein said main support layer comprises tissue.

9. An absorbent composite for absorbing liquids, said absorbent composite comprising:

a paper or non-woven fabric main support layer;

a layer of absorbent material positioned on said main support layer;

said absorbent material comprising a superabsorbent granular component;

at least a first portion of said superabsorbent granular component being intimately bonded to said main support layer;

an adhesive, applied by spraying from the melt state, for gluing at least said first portion of said superabsorbent granular component to said main support layer;

an intermediate support layer having a second portion of said superabsorbent granular component bonded thereto and a cover layer enclosing said intermediate support layer.

10. An absorbent composite according to claim 9, wherein said first portion of said superabsorbent granular component is arranged in a layer such that the granules of said granular component form a single layer within a common plane.

11. An absorbent composite according to claim 9, wherein said first portion of said superabsorbent granular component has smaller granules than said second portion of said superabsorbent granular component.

12. An absorbent composite according to claim 11, wherein said second portion of said superabsorbent component is glued to said intermediate support layer with an adhesive.

13. An absorbent composite for absorbing liquids, said absorbent composite comprising:

a paper or non-woven fabric main support layer;

a layer of absorbent material positioned on said main support layer;

said absorbent material comprising a superabsorbent granular component;

at least a first portion of said superabsorbent granular component being intimately bonded to said main support layer;

an adhesive, applied by spraying from the melt state, for gluing at least said first portion of said superabsorbent granular component to said main support layer;

a cover layer positioned opposite said main support layer for covering said superabsorbent component; and a cover strip positioned on top of said cover layer.

14. An absorbent composite according to claim 13, wherein said cover layer is comprised of non-woven material.

15. An absorbent composite according to claim 14, wherein said non-woven material is comprised of at least 20% of viscose and at most 80% of polypropylene.

16. An absorbent composite according to claim 14, wherein said non-woven material is comprised of tissue.

17. An absorbent composite according to claim 14, wherein said non-woven material is comprised of 100% viscose.

18. An absorbent composite according to claim 16, wherein said viscose is hydrophilic.

19. An absorbent composite according to claim 13, wherein said cover strip is comprised of non-woven material having a hydrophobic inner side facing said cover layer.

20. An absorbent composite according to claim 19, wherein said non-woven material is comprised of at least 80% of polypropylene and at most 20% of viscose.

21. An absorbent composite according to claim 19, wherein said non-woven material is comprised of 100% viscose.

22. An absorbent composite according to claim 21, wherein said viscose is hydrophilic.

23. An absorbent composite for absorbing liquids, said absorbent composite comprising:

a paper or non-woven fabric main support layer;

a layer of absorbent material positioned on said main support layer;

said absorbent material comprising a superabsorbent granular component;

at least a first portion of said superabsorbent granular component being intimately bonded to said main support layer;

an adhesive, applied by spraying from the melt state, for gluing at least said first portion of said superabsorbent granular component to said main support layer; and a substantially moisture-impermeable outer shell positioned exterior to said main support layer.

24. An absorbent composite according to claim 23, wherein said outer shell is made of a material selected from the group consisting of polypropylene and amylose.

25. An absorbent composite for absorbing liquids, said absorbent composite comprising:

a paper or non-woven fabric main support layer;

a layer of absorbent material positioned on said main support layer;

said absorbent material comprising a superabsorbent granular component;

at least a first portion of said superabsorbent granular component being intimately bonded to said main support layer; and an adhesive, applied by spraying from the melt state, for gluing at least said first portion of said superabsorbent granular component to said main support layer;

wherein said main support layer is substantially moisture-impermeable.

26. An absorbent composite according to claim 25, wherein said main support layer is made of a material selected from the group consisting of polypropylene and amylose.

* * * * *